US00PP14561P29

(12) United States Plant Patent
Kolster

(10) Patent No.: US PP14,561 P2
(45) Date of Patent: Feb. 24, 2004

(54) SYMPHORICARPOS PLANT NAMED 'KOLMSNO'

(50) Latin Name: *Symphoricarpos albus*
Varietal Denomination: Kolmsno

(75) Inventor: Peter Rudolf Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/421,345

(22) Filed: Apr. 23, 2003

(51) Int. Cl.[7] ..... A01H 5/00
(52) U.S. Cl. ..... Plt./226
(58) Field of Search ..... Plt./226

(56) References Cited

U.S. PATENT DOCUMENTS

PP13,204 P2 * 11/2002 de Jong ..... Plt./226
PP13,206 P2 * 11/2002 van Leyssen ..... Plt./226
PP13,244 P2 * 11/2002 de Jong ..... Plt./226
2003/0150029 P1 * 8/2003 Arisz ..... Plt./226

OTHER PUBLICATIONS

UPOV ROM GTITM Computer Database GTI Jouve Retrival Software 2203/04 Citation for "Kolmsno".*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Symphoricarpos plant named 'Kolmsno', characterized by its upright and somewhat outwardly spreading plant habit; freely branching growth habit; dark green leaves; white-colored fruits; and good postproduction longevity.

2 Drawing Sheets

Botanical classification/cultivar designation: *Symphoricarpos albus* cultivar Kolmsno.

BACKGROUND OF THE INVENTION

The present Invention relates to a new and distinct cultivar of Symphoricarpos plant, botanically known as *Symphoricarpos albus*, commercially used as cut stems with fruits, and hereinafter referred to by the name 'Kolmsno'.

The new Symphoricarpos is a product of a planned breeding program conducted by the Inventor in Boskoop, The Netherlands. The objective of the breeding program was to develop cut Symphoricarpos cultivars with attractive fruit coloration.

The new cultivar originated from a cross made by the Inventor in 1998 of two unidentified proprietary seedling selections, not patented. The cultivar Kolmsno was discovered and selected by the Inventor in 2000 as a flowering plant within the progeny of the stated cross in a controlled environment in Boskoop, The Netherlands.

Asexual reproduction of the new Symphoricarpos by terminal cuttings taken at Boskoop, The Netherlands, has shown that the unique features of this new Symphoricarpos are stable and reproduced true to type in successive generations of asexual reproduction.

SUMMARY OF THE INVENTION

The following traits have been repeatedly observed and are determined to be the unique characteristics of 'Kolmsno'. These characteristics in combination distinguish 'Kolmsno' as a new and distinct cultivar:

1. Upright and somewhat outwardly spreading plant habit.
2. Freely branching growth habit.
3. Dark green-colored leaves.

4. White-colored fruits.
5. Good postproduction longevity.

Plants of the new Symphoricarpos differ from plants of the parent seedling selections primarily in growth habit and fruit coloration.

Plants of the new Symphoricarpos can be compared to plants of the Symphoricarpos cultivar White Hedge, not patented. In side-by-side comparisons conducted in Boskoop, The Netherlands, plants of the new Symphoricarpos differed from plants of the cultivar White Hedge in the following characteristics:

1. Plant of the new Symphoricarpos were more upright than plants of the cultivar White Hedge.
2. Plants of the new Symphoricarpos were more freely branching than plants of the cultivar White Hedge.
3. Plants of the new Symphoricarpos had darker green-colored leaves than plants of the cultivar White Hedge.

BRIEF DESCRIPTION OF THE PHOTOGRAPHS

The accompanying colored photographs illustrate the overall appearance of the new Symphoricarpos, showing the colors as true as it is reasonably possible to obtain in colored reproductions of this type. Colors in the photographs may differ slightly from the color values cited in the detailed botanical description which accurately describe the colors of the new Symphoricarpos.

The photograph at the top of the first sheet comprises a side perspective view of a typical plant of 'Kolmsno'.

The photograph at the bottom of the first sheet is a close-up view of a typical stem and leaves of 'Kolmsno'.

The photograph at the top of the second sheet comprises a close-up view of typical flowers of 'Kolmsno'.

The photograph at the bottom of the second sheet comprises a close-up view of typical fruits of 'Kolmsno'.

DETAILED BOTANICAL DESCRIPTION

The new Symphoricarpos has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about two years old and pruned annually during the spring. The photographs and description were taken during the summer when outdoor day temperatures ranged from 7 to 30° C. and night temperatures ranged from 3 to 16° C. In the following description, color references are made to The Royal Horticultural Society Colour Chart, 2001 Edition, except where general terms of ordinary dictionary significance are used.

Botanical classification: *Symphoricarpos albus* cultivar Kolmsno.

Parentage:

*Female parent.*—Unidentified proprietary selection of *Symphicarpos albus*, not patented.

*Male parent.*—Unidentified proprietary selection of *Symphoricarpos albus*, not patented.

Propagation:

*Type.*—Terminal cuttings.

*Time to produce rooted cutting.*—Summer: About 20 days at 20° C. Winter: About 40 days at 12° C.

*Time to produce a rooted young plant.*—About 90 days at 20° C.

*Root description.*—Freely branching; medium thickness; light brown in color.

Plant description:

*Plant form.*—Upright and somewhat outwardly spreading perennial shrub; inverted triangle.

*Growth habit.*—Moderately vigorous. Freely branching; dense and bushy growth habit.

*Growth rate.*—Plants grow about 15 cm per month during the spring in Boskoop, The Netherlands.

*Plant height.*—About 100 cm.

*Plant width* (*spread*).—About 100 cm.

*Quantity of stems per year.*—About 15.

*Lateral branches.*—Length: About 26 cm. Diameter: About 1.5 mm. Internode length: About 3.2 cm. Strength: Strong. Texture: Smooth; glabrous. Color, immature: 146B. Color, mature: 199A to N199A.

*Foliage description.*—Leaves opposite, simple and generally symmetrical. Length: About 3.4 cm. Width: About 2.4 cm. Shape: Ovate to elliptic. Apex: Acute. Base: Attenuate to rounded. Margin: Developing leaves, mostly entire; fully expanded leaves with shallow lobing. Texture, upper and lower surfaces: Glabrous; slightly rugose. Venation pattern: Pinnate. Color: Developing leaves, upper surface: Between 141A and 143A. Developing leaves, lower surface: 138B. Fully expanded leaves, upper surface: 139A. Fully expanded leaves, lower surface: 138A to 191A. Venation, upper surface: 143A to 143B. Venation, lower surface: 144D. Petiole: Length: About 5 mm. Diameter: About 1 mm. Color, upper and lower surfaces: 143A to 143B.

Flower description:

*Flower type and habit.*—Single campanulate flowers arranged in terminal and axillary clusters with about 13 flowers per cluster. Flowers faintly fragrant; sweet. Flowers not persistent. Flowers face outward to slightly drooping.

*Natural flowering season.*—Typically July to early September in Boskoop, The Netherlands.

*Postproduction longevity.*—Cut stems are typically harvested when all flowers have developed fruits. Flowers last about three to five days on the plant. Postproduction longevity of cut stems with fruits is about two weeks.

*Flower cluster height.*—About 1.8 cm.

*Flower cluster diameter.*—About 2.1 cm.

*Flower buds.*—Height: About 5 mm. Diameter: About 3.5 mm. Shape: Orbicular. Color: 183C to 183D.

*Flowers.*—Diameter: About 8 mm. Depth: About 6 mm.

*Petals.*—Quantity per flower: Five. Length: About 6 mm. Width: About 3 mm. Shape: Elliptic. Apex: Acute. Base: Fused. Margin: Entire. Texture, upper surface: Pubescent. Texture, lower surface: Glabrous. Color: Developing and fully opened flowers, upper surface: 63C to 63D; color does not fade with subsequent development. Developing and fully opened flowers, lower surface: 186A.

*Sepals.*—Quantity per flower: Five. Length: About 4 mm. Width: About 1 mm. Shape: Linear. Apex: Acuminate. Base: Fused. Margin: Entire. Texture, upper and lower surfaces: Smooth; glabrous. Color: Developing and fully expanded sepals, upper surface: 143A. Developing and fully expanded sepals, lower surface: 143B; towards the apex, 178A to 178B.

*Peduncles.*—Length: About 1.1 cm. Diameter: About 1 mm. Orientation: Erect. Strength: Moderately strong. Color: 143B.

*Pedicels.*—Length: About 1.5 mm. Diameter: About 1 mm. Orientation: About 40 to 90° from vertical. Strength: Moderately strong. Color: 143B.

*Reproductive organs.*—Stamens: Quantity per flower: About five. Anther shape: Narrowly oblong. Anther length: About 1.5 mm. Anther color: 4C to 4D. Pollen amount: Scarce. Pollen color: 4C. Pistils: Quantity per flower: One. Pistil length: About 3.5 mm. Stigma shape: Club-shaped. Stigma color: 143A to 143B. Style length: About 3 mm. Style color: 145D. Ovary color: 143B.

*Fruits.*—Quantity per flower: One. Days to ripening: About 30. Type: Berry. Shape: Spherical. Length: About 1.5 cm. Diameter: About 1.4 cm. Texture: Smooth; glabrous. Color: 155C, blushed with 145D; slightly glossy.

*Seeds.*—Quantity per fruit: About two per fruit. Length: About 5 mm. Diameter: About 3 mm. Texture: Smooth; glabrous. Color: 155D.

Disease/pest resistance: Plants of the new Symphoricarpos have not been observed to be resistant to pathogens and pests common to Symphoricarpos.

Temperature tolerance: Plants of the new Symphoricarpos have been observed to tolerate temperatures ranging from −20 to 35° C.

It is claimed:

1. A new and distinct cultivar of Symphoricarpos plant named 'Kolmsno', as illustrated and described.

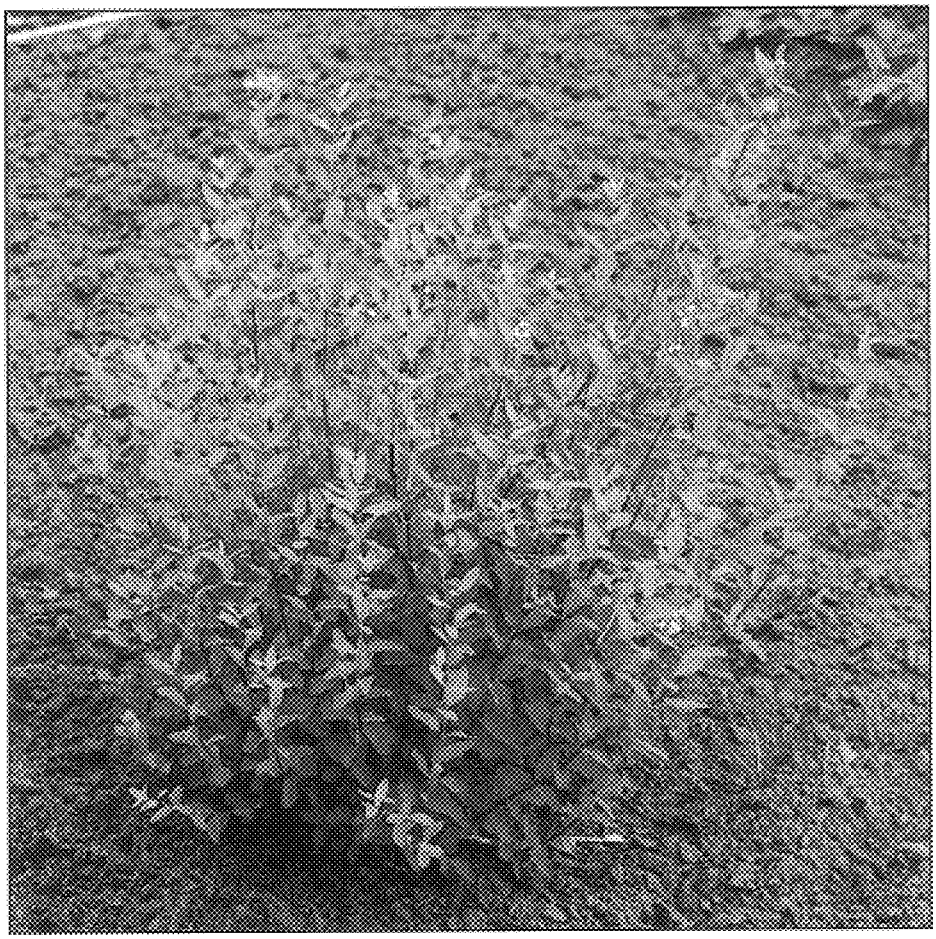
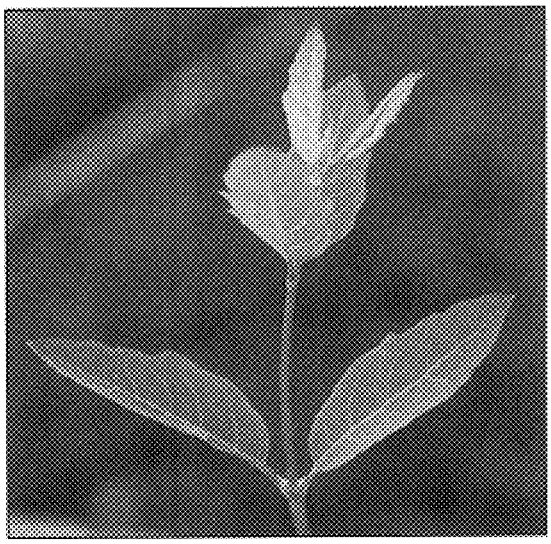

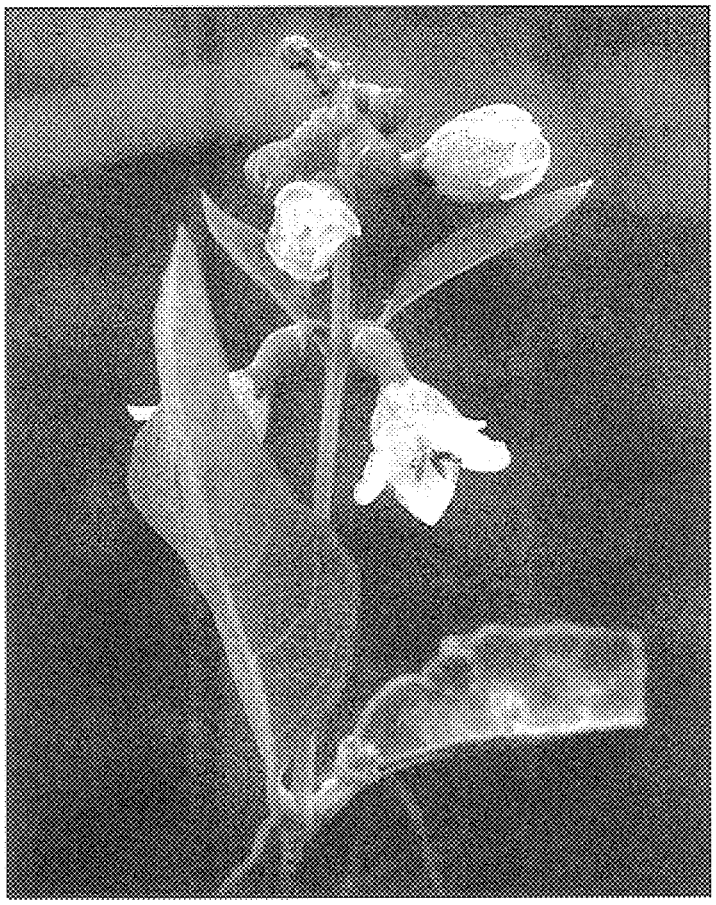
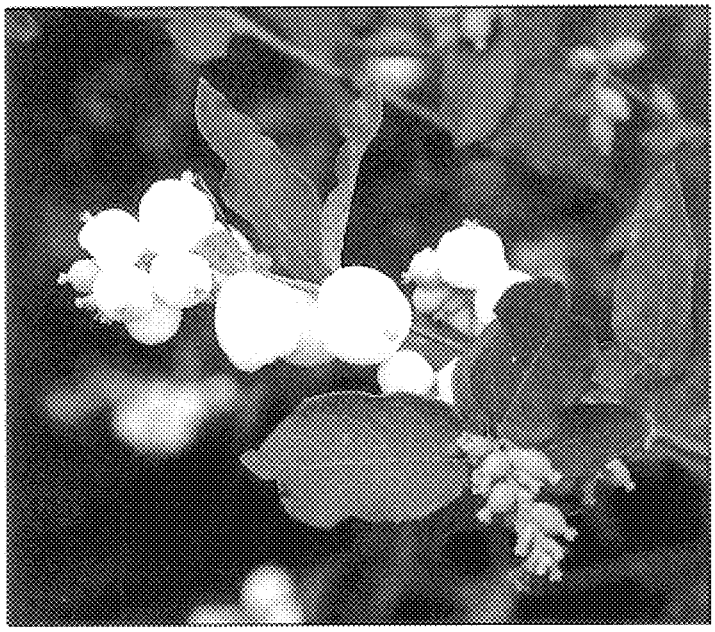

* * * * *